(12) United States Patent
Grayson et al.

(10) Patent No.: US 9,333,269 B2
(45) Date of Patent: May 10, 2016

(54) POLYPLEX GENE DELIVERY VECTORS

(75) Inventors: Scott Grayson, New Orleans, LA (US); Mallory Cortez, New Orleans, LA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 634 days.

(21) Appl. No.: 13/635,640

(22) PCT Filed: Mar. 21, 2011

(86) PCT No.: PCT/US2011/029180
§ 371 (c)(1),
(2), (4) Date: Dec. 26, 2012

(87) PCT Pub. No.: WO2011/116371
PCT Pub. Date: Sep. 22, 2011

(65) Prior Publication Data
US 2013/0115699 A1    May 9, 2013

Related U.S. Application Data

(60) Provisional application No. 61/315,558, filed on Mar. 19, 2010.

(51) Int. Cl.
| C07D 487/06 | (2006.01) |
| A61K 48/00 | (2006.01) |
| C07C 247/04 | (2006.01) |
| C08G 73/02 | (2006.01) |
| C12N 15/88 | (2006.01) |

(52) U.S. Cl.
CPC ............ *A61K 48/0041* (2013.01); *C07C 247/04* (2013.01); *C07D 487/06* (2013.01); *C08G 73/0206* (2013.01); *C12N 15/88* (2013.01)

(58) Field of Classification Search
None
See application file for complete search history.

(56) References Cited

U.S. PATENT DOCUMENTS

| 2003/0166601 A1 | 9/2003 | Woodle et al. |
| 2009/0018216 A1 | 1/2009 | Kataoka et al. |

FOREIGN PATENT DOCUMENTS

WO   2005/085443   9/2005

OTHER PUBLICATIONS

Mock. Journal of Organic Chemistry, 1989, 54(22), 5302-8.*
Guo. Bioscience Reports, 2000, 20(5), 419-432.*
Gosselin. Bioconjugate Chemistry, 2002, 13(5), 1044-53.*
Cortes. Polymer Preprints, 2010 51(1), 466-67.*
International Search Report for PCT/US2011/029180 Mailed Nov. 18, 2011.
Written Opinion for PCT/US2011/029180 Mailed Nov. 18, 2011.
Fijten et al., "Clickable Poly(2-Oxazoline)s as Versatile Building Blocks," Macromol. Chem. Phys. vol. 209, pp. 1887-1895 (2008).
International Preliminary Report on Patentability for PCT/US2011/029180, Issued Sep. 25, 2012.

* cited by examiner

*Primary Examiner* — Noble Jarrell
(74) *Attorney, Agent, or Firm* — McBee Moore Woodward & Vanik IP, LLC

(57) ABSTRACT

Compositions comprising linear PNAI, cyclic PNAI, linear PEI, and/or cyclic PEI, useful for delivering compounds or substances into a cell, are provided, as well as methods of making linear PNAI, cyclic PNAI, linear PEI, and cyclic PEI. Also provided are methods of using compositions comprising linear PNAI, cyclic PNAI, linear PEI, and/or cyclic PEI for introducing substances into a cell.

22 Claims, 10 Drawing Sheets

Initiation

Propagation

Termination

Nu = nucleophile

POLYPLEX GENE DELIVERY VECTORS

BACKGROUND

1. Field

The present disclosure relates to intracellular delivery, and relates in particular to compositions for intracellular delivery of therapeutic agents, diagnostic agents, and other materials in the presence or absence of targeting groups. The present disclosure is directed, inter alia, to polymer compositions comprising linear PNAI, cyclic PNAI, linear PEI, and/or cyclic PEI, useful for delivering compounds or substances into a cell. The present disclosure is also directed, inter alia, to methods of using compositions comprising cyclic PNAI and/or cyclic PEI.

2. Description of Related Art

Cells are the basic structural and functional units of all living organisms. All cells contain cytoplasm surrounded by a plasma, or cell, membrane. Most bacterial and plant cells are enclosed in an outer rigid or semi-rigid cell wall. The cells contain DNA which may be arranged in 1) a nuclear membrane or 2) free in cells lacking a nucleus. While the cell membrane is known to contain naturally occurring ion channels, compounds that are therapeutically advantageous to cells are usually too large to pass through the naturally occurring ion channels. Conventional interventional methods for delivering compounds or substances into cells have proved difficult in view of the need for the compounds to pass through the cell membrane, cell wall, and/or nuclear membrane.

Molecular biology has resulted in mapping the genomes of many plants and animals, including the mapping of much of the human genome. The potential for advances in the understanding of the genetic basis of diseases is great, as is the potential for the development of therapies to treat such diseases. To fully take advantage of these advancements and treatment therapies, however, methods are needed for delivering desired compounds into the target cells. Accordingly, researchers developed a variety of intracellular delivery methods for inserting genes and other compounds into both plant and animal cells.

For example, calcium phosphate DNA precipitation has been used to deliver genetic material into cells in cell culture. However, one drawback of this method is that the transfection efficiency (the percentage of transfected cells in a given population) and subsequent gene expression is generally very low.

Improved transfection has been achieved using viral vectors (e.g., adenovirus and retrovirus), but again, difficulties with gene expression have persisted. In addition, substantial concerns regarding antigenicity and the potential of mutant viruses and other possible deleterious effects exist. For example, some viruses may integrate into the genome and facilitate stable expression. If the virus integrates in a way that disrupts normal cell function, however, adverse consequences could result (e.g., cell death, transformation, cancer, etc.).

Liposomes, manufactured more easily than viral vectors, have shown promise as gene delivery agents. Liposomes have fewer biological concerns (for example, they are generally non-antigenic) but the efficiency of transfection and gene expression using liposomes has typically been lower than with viruses.

Gene guns, or biolistic delivery systems, use heavy metal particles (e.g., gold) coated with DNA to fire the particles at high speed into cells. While gene guns have enabled gene expression in culture systems, they have not worked well in vivo. Furthermore, the blast of heavy metal particles may cause damage to the cells and may also introduce undesirable foreign materials, e.g. gold particle fragments, into the cells.

Electroporation is another method of delivering genes into cells. In this technique, pulses of electrical energy are applied to cells to temporarily create pores or openings in the cell to facilitate entry of DNA. Electroporation may damage cells, though, and has not been shown to be highly effective in vivo.

Gene therapy has been heralded as the next revolution in modern medicine, being seen as a potential cure to many diseases both inherited and acquired. Gene therapy is the delivery of genetic information, typically plasmid DNA contained in a vector, to a cell. Typically, the DNA enters the cell via endocytosis and is released into the cytoplasm. Ultimately, the DNA interacts with the host cell environment to (for example) produce proteins encoded by the DNA. One major area of study for gene therapy is the correction of inherited diseases in which a genetic disorder stemming from a malfunctioning endogenous gene may be attenuated by a "healthy" exogenous gene. As a result of extensive genomic research, the genetic makeup of many diseases and their healthy counterparts have been deduced (e.g., cystic fibrosis, Huntington's disease, Alzheimer's disease, and sickle cell anemia), which has spurred on further gene transfer research. The primary obstacle still standing in the way of successful treatment is delivery; it must be cell specific, the gene transfer must be efficient, and the vector must be non-toxic (Putnam, D. "Polymers for Gene Delivery Across Length Scales" *Nature Materials Vol.* 5 June 2006: 439-451).

The first and most developed area of gene transfer research has utilized viral vectors to introduce DNA. This area has produced some positive results, though the vector itself is inherently flawed. Viruses have evolved the ability to use the host cell's own replication machinery to efficiently and rapidly replicate their own genetic information, which often results in the death of the host cell. To get around this problem, viruses used for transfection are genetically modified to be replication defective. This requires the removal of its virulent genetic information and the insertion of a therapeutic gene. The initial results from early clinical trials using this technique were positive, but early success was soon diminished when three cases of leukemia-like complications were detected in participants of a clinical trial (Wong, S. Y., J. M. Pelet, D. Putnam. "Polymer systems for gene delivery—Past, Present, and Future" *Progress in Polymer Science Vol.* 32 April. 2007: 99-837). The virus's random transgenic insertion of its genetic payload into the host cell chromosome was to blame, since it could potentially insert into an area that coded for a protein responsible for the regulation of cell growth and division. Other potentially lethal complications that may occur using a viral vector include initiation of an immunological response by the host, as well as the potential for the vector to travel to disease-free tissue.

The clarification and correction of these complications has become a major area of interest in this field. At the same time many have turned to non-viral delivery systems to find a safer method of gene delivery, including delivery of naked DNA by physical methods, lipid based vectors, and synthetic polymer vectors (Taira, K., K. Kataoka, T. Niidome. *Non-viral Gent therapy: Gene Design and Delivery.* Tokyo, New York Springer Science & Business Media, 2005). Delivery of free plasmid DNA via electoporation into a cell has been an enticing approach, given the absence of an immune response that is more evident in molecular vector systems. Electroporated DNA is induced to enter a cell by an application of electric or magnetic fields to the targeted tissue, which increases the permeability of cell membranes. Although this is one of the most precise methods to target a certain tissue, it is not cell specific and requires high levels of unencapsulated DNA, which has been shown to lead to high blood pressure and slow heart rates (Taira, K, 2005). An alternative method is to form hydrophobic lipoplexes, liposomes that associate with DNA, which are more readily taken up through interactions with the cell's phospholipid bilayer. Combined with the addition of a ligand or signaling sequence, these vectors can be more efficient at entering targeted cells.

Payload as well as transfection efficiency have been shown to increase when lipid based delivery is used in conjunction with cationic polymers (Wong, S. Y., 2007). Charged polymers, such as polyethylenimine (PEI), have been incorporated into vector systems called polyplexes, which have become popular because of their ability to be manipulated in the laboratory to achieve desired characteristics; however some obstacles still stand in the way. A current challenge in the design of cationic vectors is overcoming cytotoxicity. A number of researchers have studied the effects of adding further modifications to enhance biocompatibility. The exact mechanism that causes cytotoxicity is not entirely certain, but the leading hypothesis is that ionic interactions between the cationic moieties of the vector and the anionic domains on the cell surface lead to polyplex aggregation on the outer plasma membrane (Wong, S. Y., 2007). The cytotoxic effect has been shown to be caused and exacerbated by several physical properties including molecular weight (MW), degree of branching, charge density, cationic functionality type, three dimensional conformation, as well as polyplex size, surface area and flexibility (Wong, S. Y., 2007). Of the different properties that increase toxicity, MW has been shown to be one of the leading parameters. This has posed a crucial dilemma, since increasing the MW within a certain limit is also beneficial to transfection efficiency (Wong, S. Y., 2007). Other problems that arise when using cationic vectors include introducing DNA into non-target cells, and the systemic stability of the polyplex in the blood stream.

The present disclosure provides new and/or better methods for delivering compounds, including genetic material, into a cell. The methods of the present disclosure provide a significant advantage over prior art methodology in that enhanced levels of intracellular delivery and—in the case of nucleotides—gene expression may be achieved. In addition, the methods of the present disclosure may be performed in cell lines which may be otherwise resistant to intracellular delivery and gene expression using other conventional means. These and/or other aspects of the present disclosure will become apparent from the further discussions herein.

BRIEF SUMMARY

The present disclosure provides polymer compositions useful for delivering compounds into a cell. More particularly, the polymer compositions comprise cyclic PNAI and/or cyclic PEI.

The present disclosure also provides methods of delivering at least one compound or substance (including, without limitation, nucleic acids and/or small-molecule pharmaceuticals) into a cell comprising administering to the cell a composition comprising said at least one compound to be delivered and a cyclic PNAI, a cyclic PEI, or combinations thereof.

In addition, the present disclosure provides methods of treating a patient comprising administering to said patient a composition comprising a therapeutically effective amount of a compound and a cyclic PNAI, a cyclic PEI, or combinations thereof.

The subject disclosure provides methods of effecting the expression of at least one nucleotide sequence in a cell comprising administering to said cell a composition which comprises a said at least one nucleotide sequence and a cyclic PNAI, a cyclic PEI, or combinations thereof.

If desired, the compositions may further comprise a carrier.

Also included in the present disclosure are compositions and kits comprising, for example, a therapeutically effective or diagnostically effective amount of a compound to be delivered, a cyclic PNAI and/or a cyclic PEI and/or a carrier, and, in the case of a kit, optionally other conventional kit components.

These, as well as other, aspects of the invention are set forth in greater detail below.

The present disclosure provides a compound selected from the group consisting of:

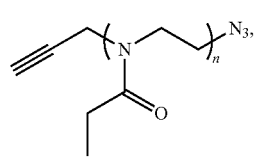

Formula 7

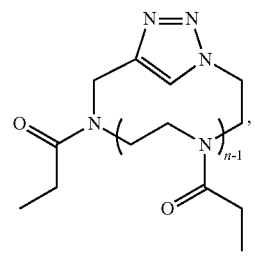

Formula 8

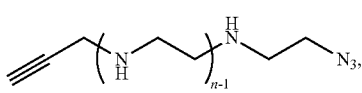

Formula 9

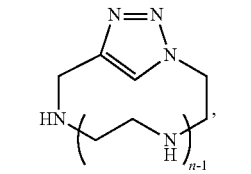

Formula 10 and combinations thereof, wherein n is an integer from 1 to 750. In one aspect, n is an integer from 1 to 500. In one aspect, n is an integer from 1 to 250. In one aspect, n is an integer from 1 to 200. In one aspect, n is an integer from 1 to 150. In one aspect, n is an integer from 1 to 120. In one aspect, n is an integer from 10 to 120. In one aspect, n is an integer from 10 to 100. In one aspect, n is an integer from 25 to 75. In one aspect, said compound corresponds to Formula 7. In one aspect, said compound corresponds to Formula 8. In one aspect, said compound corresponds to Formula 9. In one aspect, said compound corresponds to Formula 10. In one aspect, said compound corresponds to a combination of Formulae 7, 8, 9, and 10.

The present disclosure provides a method of producing a linear PNAI, the method comprising: combining propargyl toluene-4-sulfonate with 2-ethyl-2-oxazoline; and adding sodium azide to said combination, thereby producing said linear PNAI.

The present disclosure provides a method of producing a cyclic PNAI, the method comprising: precipitating the linear PNAI described above; and adding said precipitated linear PNAI to a Cu(I)Br/PMDETA/CHCl$_2$ solution, thereby producing cyclic PNAI.

The present disclosure provides a method of producing a linear PEI, the method comprising: precipitating the linear PNAI described above; and performing acid reflux of said cyclic PNAI, thereby producing a linear PEI.

The present disclosure provides a method of producing a cyclic PEI, the method comprising: producing a cyclic PNAI as provided above; and performing acid reflux of said cyclic PNAI, thereby producing a cyclic PEI.

The present disclosure provides a method of introducing a substance into a cell, the method comprising: mixing said substance with: linear PNAI; cyclic PNAI; linear PEI; cyclic PEI; or a combination thereof, and exposing said cell to said mixture, thereby introducing said substance into said cell. In one aspect, the substance is a nucleic acid sequence. In one aspect, the introducing of a nucleic acid sequence effects the expression of a protein encoded by said nucleic acid sequence. In one aspect, the introducing of a nucleic acid sequence suppresses the expression of a protein. In one aspect, the substance is a drug. In one aspect, the cell is a prokaryotic cell. In one aspect, the cell is a eukaryotic cell. In one aspect, the cell is an animal cell. In one aspect, the cell is a mammalian cell. In one aspect, the cell is a yeast cell, a bacterial cell, or a plant cell.

The present disclosure provides a method of producing cyclic PNAI, the method comprising: combining a compound of the formula R—X with 2-ethyl-2-oxazoline; adding a nucleophile to said combination to produce linear PNAI; precipitating linear PNAI; and adding said linear PNAI to a solution comprising Cu(I)Br and PMDETA, thereby producing cyclic PNAI. In an aspect of this embodiment, R may be selected from Formula 1 or Formula 2, below. In an aspect of this embodiment, X may be selected from Formula 3 (below), Formula 4 (below), Br$^-$, or I$^-$. In an aspect of this embodiment, the nucleophile may be selected from NaN$_3$ and NaSH.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Figure 1:
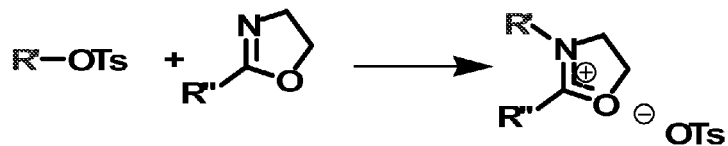
FIG. 1 shows Scheme 1, the synthesis of PNAI utilizing different end groups. A strong nucleophile is used to terminate the reaction.
Figure 1:
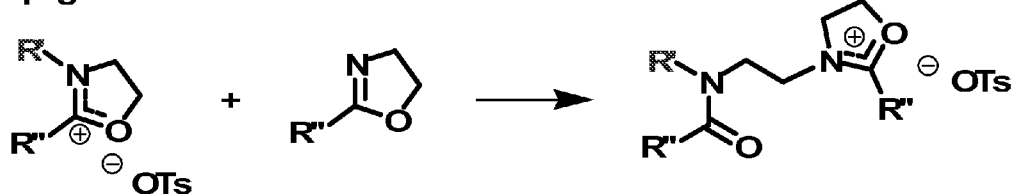
Figure 1:
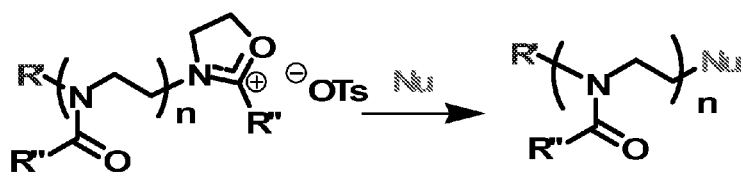

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

In the past two decades, ligand-conjugated polymer based (polyplex) gene delivery has been utilized with increasing efficiency. Polymer vectors have gained much attention from the gene delivery and pharmaceutical community because their physiochemical properties are well understood, and they can be modified in the laboratory. The ability to change a vector's physical makeup—e.g., by altering its side chain composition, polydispersity, and molecular weight to increase payload efficiency and decrease cytotoxicity—has become a main focus of interest in this field. Construction of polymer vector libraries which contain polymers that vary slightly in their composition is an empirical method to categorize and test for desired properties. The present disclosure provides methods for polymerization of 2-ethyl-2-oxazoline to form poly(N-acylethylenimine) (PNAI) with functional azide and alkyne terminal end groups that are covalently bonded using a "click" chemistry intramolecular reaction to synthesize cyclic architectures. The present disclosure also provides uses for the same. The subsequent hydrolysis of the side chains provides a new architecture of poly(ethyleneimine) (PEI) for gene delivery.

To form a polyplex, cationic monomers are polymerized into long chains which are capable of encapsulating naked DNA by electrostatic interactions arising from DNA's negatively charged phosphodiester backbone. The polymer first condenses DNA to a size that is sufficient for cellular uptake, which is dependent on its nitrogen to phosphate charge ratio (Wong, S. Y., 2007). This also determines how well the cationic polymer will associate with the vector. Enroot to the target cell, the vector must not lose its cargo but once it reaches a desired location within the cell the DNA must dissociate. Upon reaching a cell, entry can be accomplished by several methods mediated by cellular endocytosis. Vectors equipped with specific internalizing sequences or ligands can be used in a cell specific manner to internalize them. Non-specific methods include ionic interactions with proteoglycans bound to cell membranes to stimulate endocytosis or the inclusion of lipophilic residues capable of interacting with the cell membrane as described earlier. Here again, polyplex size is crucial to cellular uptake with optimal sizes differing between various cells. Once internalized, the vector must continue to protect the cargo from degradation; a major threat of this comes from lysosomes. Clathrin mediated endocytosis, which directs shuttling through the endo-lysosomal pathway, has been one pathway studied for internalizing polyplexes (Wong, S. Y., 2007). The exact mechanism for lysosomal escape has not been fully elucidated. However, some researchers have inferred that by incorporating amine groups into the polymer, it becomes capable of absorbing protons in the low pH environment of the endo-lysosome; this may cause the organelle to burst due to osmotic pressure releasing the endocytosed material into the cytosol. Once in the cytosol, endogenous cytosolic factors are commonly incorporated to move either the polyplex or the naked DNA to the nucleus where nuclear localizing signals can then be used to gain entry (Wong, S. Y., 2007). Finally, vector dissociation and gene expression must occur for gene transfer to be successful.

Several polymers have been studied for the task of encapsulating and delivering DNA. Some of those most extensively used include PEI, poly-L-lysine, cationic dendrimers, and arginine-rich proteins (Taira, K., 2005). They all share a common characteristic in that they possess an amine functional group which is used to condense the DNA. PEI has become one of most studied polymer vector systems and has paved the way for much of what we know about cationic vectors. Commercially available PEI is synthesized through a one step ring opening polymerization of aziridine, which produces a highly branched molecule (Ham, G. E. "Polymeric Amines and Ammonium Salts"; Goethals, E. J., Ed., Pergamon Press; Elmsford, N.Y., 1980; p. 1), whose excessive random branching has been shown to increase cytotoxicity while at the same time elevate DNA binding efficiency (Feijen, J., Z. Zhong. "Low molecular weight linear polyethylenimine-b-poly(ethylene glycol)-b-polyethylenimine triblock copolymers: synthesis, characterization, and in vitro gene transfer properties" *Biomacromolecules*, 2005: 6, 3440-3448; Jeong, J. H., S. H. Song, D. W. Lim, H. Lee, T. G. Park. "DNA Transfection using Linear Poly(ethylenimine) Prepared by Controlled Acid Hydrolysis of Poly(2-ethyl-2-oxazoline)" *Journal of Controlled Release*, 2001: 73, 391-399; Fischer, D.; Li, Y.; Ahlemeyer B.; Krieglstein J.; Kissel, T.; *Biomaterials*. 2003, 24, 1121-1131; Lv, H.; Zhang, S.; Wang, B.; Cui, S.; Yan, J.; *J. Control Release*. 2006, 114, 100-109; Wightman, L.; Kircheis, R.; Rossler, V.; Carotta, S.; Ruzicka, R.; Kursa, M.; et al. *J. Gene Med.*, 2001, 3, 362-372; and Petersen, H.; Kunath, K.; Martin, A.; Stolnik, S.; Roberts, C. J.; Davies, M.; Kissel, T. Biomacromolecules, 2002, 3, 923-936). It is clear that PEI's buffering capabilities play an important role in transfection, yet the exact mechanism is not fully elucidated and further research in this area is needed (Brissault, B., K. Antoine, G. Christine, L. Christian, D. Olivier, C. Herve. "Synthesis of linear polyethylenimine drivatives for DNA transfection" *Bioconjugate Chemistry*, (2003): 14, 581-587). What is evident is that PNAI has a well defined degree of polymerization, low polydispersity, relatively simple preparation and high versatility depending on the initiator and terminator used during polymerization which has made it highly coveted within the fields of medicine, materials science and technology (Aoi, K., M. Okada. "Polymerization of Oxazolines" *Polymer Science*, 1996: 151-208; and Einzmann, M., W. Binder. "Novel Functional Initiators for Oxazoline Polymerization" *Journal of Polymer Science Part A: Polymer Chemistry*, May 2001: 2821-2831). Previous investigations into vector design demonstrates that neither highly branched nor pure linear polymers work efficiently as polyplexes indicating that the most optimal architecture most likely lies in-between the two extremes (Tang, M. X., C. T. Redemann, F. C. Szoka. "In Vitro Gene Delivery by Degraded Polyamidoamine Dendrimers" *Bioconjugate Chemistry Vol.* 7 November 1996: 703-714; Feijen, J., 2005; and Jeong, J. H., 2001). It has also been shown that molecular weight affects the efficiency of PEI (Godbey, W. T., Wu, K. K., Mikos, A. G. "Size Matters: Molecular Weight Affects the Efficiency of Poly(ethylenimine) as a Gene Delivery Vehicle" *Journal of Biomedical Materials Research Vol.* 451999: 268-275). This has led many in the field to realize that systematic studies of polymer architecture must be undertaken by developing well characterized synthetic routes which yield readily reproducible products. A novel approach to synthesizing complex but well defined architecture is to first polymerize 2-ethyl-2-oxazoline to form linear poly(N-acethylenimine) (PNAI) with terminal ends that can be further processed into various architectures. Then, through acid hydrolysis of PNAI's side chains, it is possible to obtain PEI of new and potentially therapeutic designs.

The polymerization chemistry of 2-substituted oxazolines shows wide versatility depending on the nature of monomers, initiators, and terminating agents (Kobayashi, S; Tokuzawa, T; Saegusa, T; *Macromolecules* 1982, 15, 707-710; Kirlabil, H; Yagci, Y; *Turk J Chem,* 2004, 38, 477-485; and Einzmann, M., 2001). Oxazolines are heterocyclic imino ether compounds, 2-oxazolines being five membered hererocyclic imino ether compounds or imidates. The general polymerization reaction of 2-oxazolines follows a living mechanism leading to well-defined polymerizations and low polydispersities (Aoi, K., 1996). Oxazoline polymers are amenable to a range of applications in both medicine and materials due to their low toxicity ($LD_{50}$<4 g/kg) and high hydrophilicity (Wong, S. Y., 2007). Oxazolines are also used in materials science as nonionic polymer surfactants, and polymer networks (including hydrogels) (Aoi, K., 1996).

2-oxazolines are polymerized via a cationic ring-opening polymerization to produce the corresponding derivatives of poly(N-acylethylenimine) (PNAI) (Aoi, K., 1996). The polymerization of cyclic imino ethers is thermodynamically favored due to the favorable isomerization of the imino ether group to the amide functionality and elimination of monomer ring strain. The cationic ring-opening polymerization of 2-oxazolines can follow either ionic or covalent mechanisms depending on the initiator utilized. Ionic initiators include Brønsted and Lewis acids, carbocations, trialkyl amonium salts, triflates, and alkyl halides while weak nucleophiles are covalent initiators. Termination occurs following the addition of a strong nucleophile or adventitious reactions with water. This versatility in initiation and termination allows for the introduction of different functionalities at either end of the polymer chain.

Cyclic polymers are a class of polymer architectures whose properties have not been vastly studied but are believed to exhibit unique topology and physical properties (Semlyen, J. A. *Cyclic Polymers,* 2nd ed.; Kluwer Academic: Dondrecht, The Netherlands, 2000). This can be attributed to the technical difficulties in preparing and purifying well-defined cyclic polymers (Laurent, B. A.; Grayson, S. M. *J. Am. Chem. Soc.* 2006, 128, 4238-4239; and Eugene, D. M.; Grayson, S. M.; *Macromolecules,* 2008, 41, 5082-5084). Typically, methods reported for the cyclization of linear polymer precursors suffer from poor yields and competing reactions (Hadjichritidis, N.; Pitsikalis, M.; Pispas, S.; Iatrou, H.; *Chem. Rem,* 2001, 101, 3747). Recently, a method preparing well defined cyclic poly(styrene) synthesized by atom transfer radical polymerization (ATRP) utilizing the Cu(I)-catalyzed 2+3 cycloaddition reaction between an azide and an alkyne has been reported (Laurent, B. A., 2006). Since the publication of this paper, many other types of cyclic polymers have been reported, including cyclic block copolymers (Eugene, D. M., 2008).

The utilization of highly efficient "click reactions", as termed by Sharpless et al. (Kolb, H. C.; Finn, M. G.; Sharpless, K. B. *Angew. Chemie, Int. Ed.* 2001, 40, 2004) has been widespread due to their high specificity, near-quantitative yields, and near-perfect fidelity in the presence of most functional groups (Matyjaszewski, K.; Gao, H.; *Macromolecules.* 2006. 39, 4960-4965). The Cu(I)-catalyzed [3+2] cycloaddition reaction between an azide and an alkyne has been the most utilized of the click reactions because it is fast, high-yielding, functional group tolerant, and compatible with a range of solvents. To utilize this type of chemistry for the synthesis of a cyclic PEI polymer, we are studying the synthesis of polymers of 2-oxazolines with both an alkyne and an azide as end groups.

Inspection of the molecular architecture and synthesis is the next important step in the development of a polymer vector system, with cyclic PNAI being a molecule never before investigated. Prior analysis of cyclic architecture has revealed that they have unique topologies and physical properties (Semlyen, J. A., 2000); however more research is needed to understand how they will behave as polyplexes. There are several reasons why cyclic architecture may be of an optimal therapeutic design for delivering a genetic payload. In comparison to the linear form, cyclic architecture has been shown to have longer systemic circulation times and to accumulate in higher concentrations within tissues (Nasongkla, N., B. Chen, N. Macaraeg, M. E. Fox, J. M. J. Frechet and F. C. Szoka. "Dependence of Pharmacokinetics and Biodistribution on Polymer Architecture: Effect of Cyclic versus Linear Polymers" *Journal of the American Chemical Society* March 2009: 3842-3843). Also their circular shape is analogous to that of plasmid DNA which may help to better encapsulate the genetic payload. In addition the cyclized form of the polymer physically takes on a smaller hydrodynamic volume that may lead to better packing and transfection ability; this will hopefully be analyzed soon by pore diffusion studies. Other biological applications could be to functionalize the side chains of cyclic PNAI to form molecules capable of carrying various drugs intracellularly.

Experimental Pathway

It has been reported that initiators containing trifluoromethanesulfonic acid esters (triflates) and p-toluenesulfonic acid esters (tosylates) give good results with respect to polydispersity and controlled molecular weight resulting in the preparation of defined telechelic polymers (Einzmann, M., 2001). The synthesis of PNAI has been studied using different initiators to have specific end groups on the polymer (FIG. 1). To synthesize a polymer with a terminal methyl group, methyl tosylate was used as an initiator, although the present disclosure also encompasses other initiators such as trifluoromethanesulfonate (triflate), I⁻, and Br⁻. For the synthesis of a cyclic PNAI, initiation can be used to introduce a terminal alkyne. To accomplish this, propargyl toluene-4-sulfonate ($C_{10}H_{10}O_3S$, propargyl p-toluenesulfonate) was obtained from Sigma-Aldrich (cat. no. 09954) and used as an initiator (see, e.g., FIG. 1, "R-OTs") with polyethyloxazoline (2-ethyl-2-oxazoline). The methyl tosylate (methyl p-toluenesulfonate) and propargyl toluene-4-sulfonate as initiators resulted in reproducible polymers with low polydispersities. Termination is achieved by the addition of a strong nucleophile (Scheme 1), such as $NaN_3$. This termination enables introduction of an azide to the PNAI either with direct addition of $NaN_3$. This reaction scheme is detailed further in EXAMPLES 1 and 2, below.

In reaction scheme 1, of FIG. 1, "R" may be selected from the following formulae:

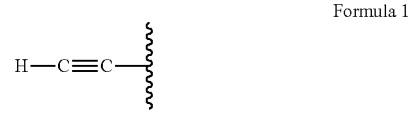

Formula 1

Formula 2

In reaction scheme 1, FIG. 1, "X" may be selected from I⁻, Br⁻, and the following formulae:

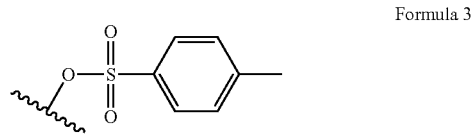

Formula 3

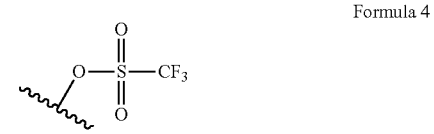

Formula 4

Figure 2:
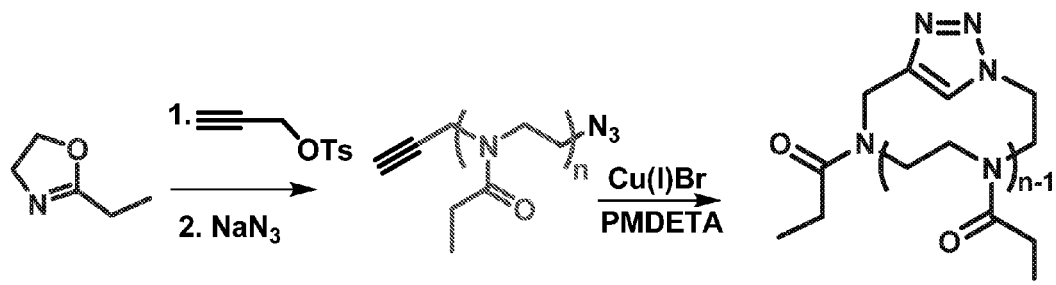
FIG. 2 shows Scheme 2, the synthesis of cyclic PNAI from an alkyne initiated and N$_3$ terminated PNAI polymer utilizing the Cu(I)-catalyzed 2+3 cycloaddition click reaction.

The "Nucleophile" of FIG. 1 could be sodium azide ($NaN_3$) or sodium hydrosulfide (NaSH). As shown in FIG. 2, using sodium azide as the nucleophile produces the coupling link shown below as Formula 5. Using sodium hydrosulfide would produce a coupling link shown as Formula 6.

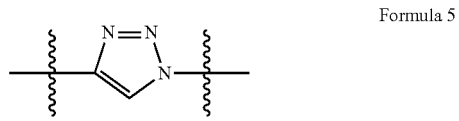

Formula 5

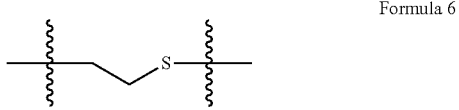

Formula 6

The cyclization (FIG. 2) of the PNAI containing alkyne and azide end groups was next preformed. PNAI was dissolved in 100 mL of DMF and in a separate flask, N,N,N',N',N-Pentamethyldiethylenetriamine (PMDETA), was dissolved in 120 mL DMF. The two solutions were degassed three times by freeze pump thaw cycles. The CuBr was added to the flask containing PMDETA and DMF while frozen. Once the two solutions were thawed, the PNAI solution was added slowly with a syringe pump at 2 mL/hr until all the solution was added. This reaction scheme is detailed in EXAMPLE 3, below.

Figure 3:
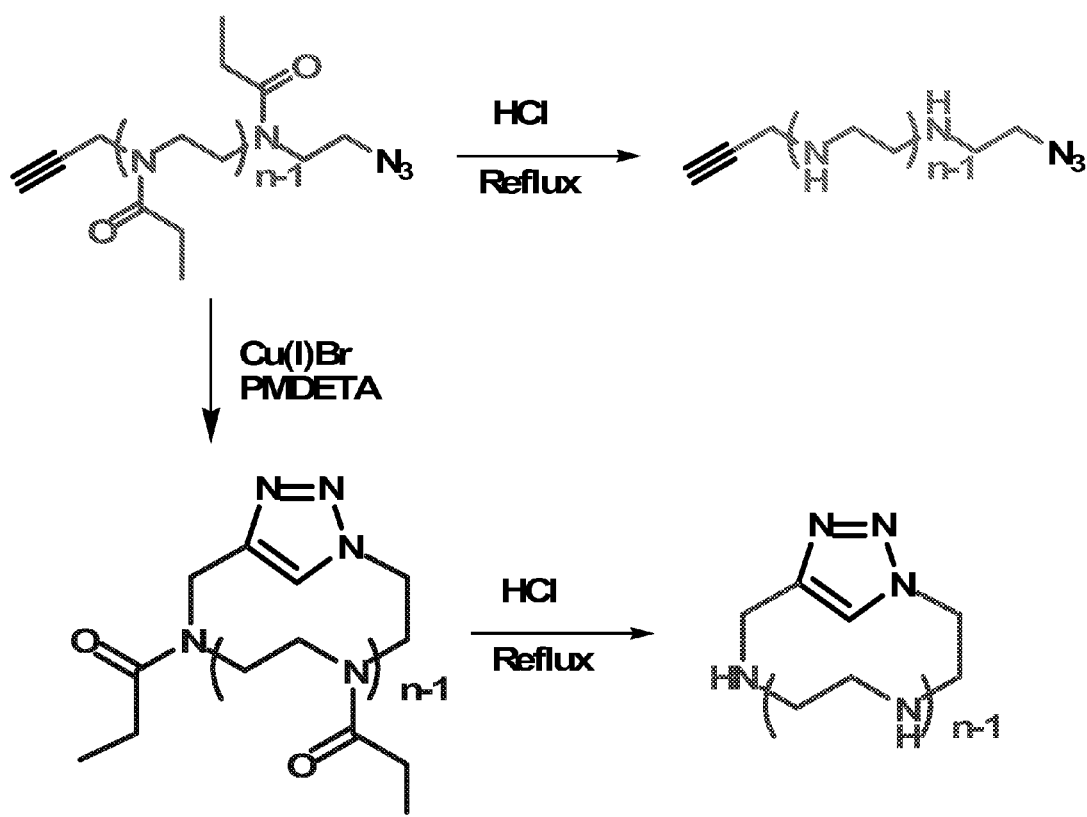
FIG. 3 shows Scheme 3, the synthesis of linear and cyclic PEI.
Figure 4:
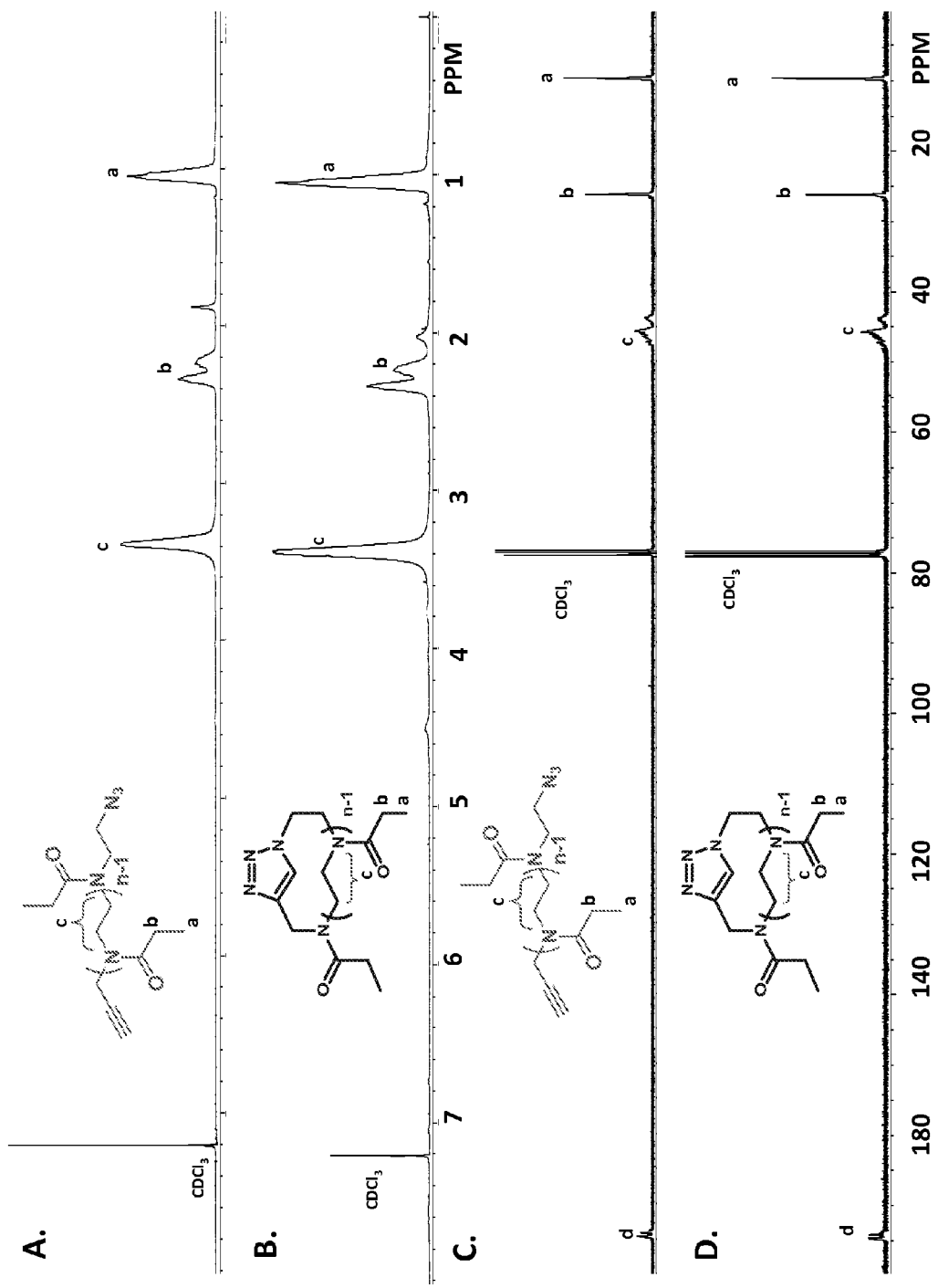
FIG. 4 shows: 4A) $^1$N NMR of linear PNAI; 4B) $^1$H NMR of cyclic PNAI; 4C) $^{13}$C NMR of linear PNAI; and 4D) $^{13}$C NMR of cyclic PNAI.
Figure 5:
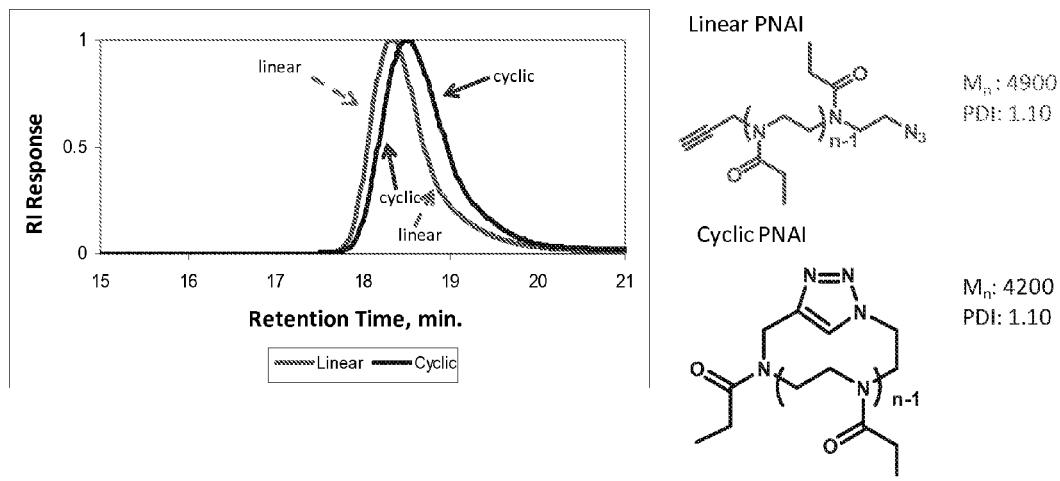
FIG. 5 is a representative example showing gel permeation chromatography (GPC) of linear and cyclic PNAI. The shift to a longer retention time for the cyclic PNAI is indicative of the change to a smaller hydrodynamic radius.
Figure 6:
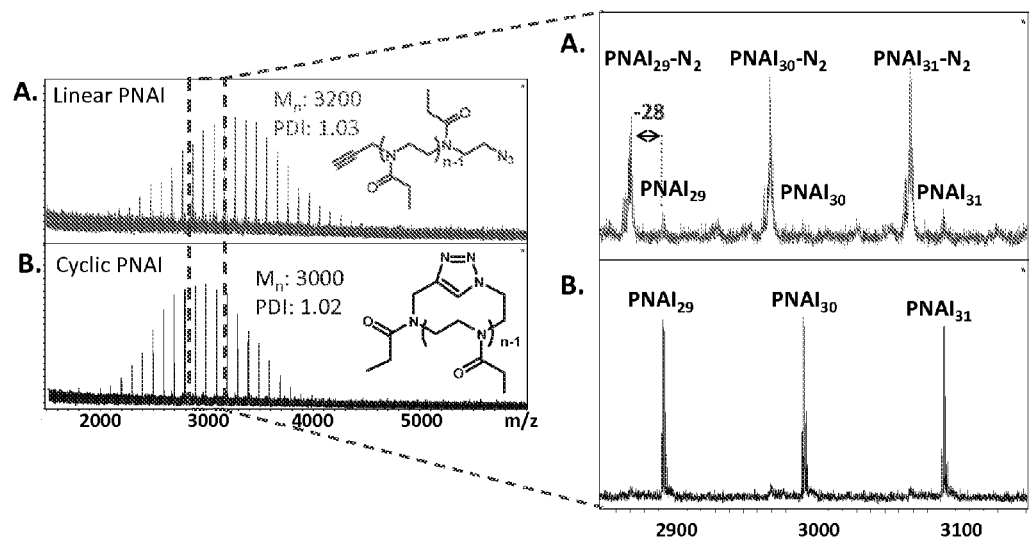
FIG. 6 is a representative example showing MALDI of: 6A) linear PNAI; and 6B) cyclic PNAI. For linear PNAI, predominately the loss of N$_2$ is observed in reflector mode. Once cyclized, the triazole ring negates the loss of N$_2$.
Figure 7:
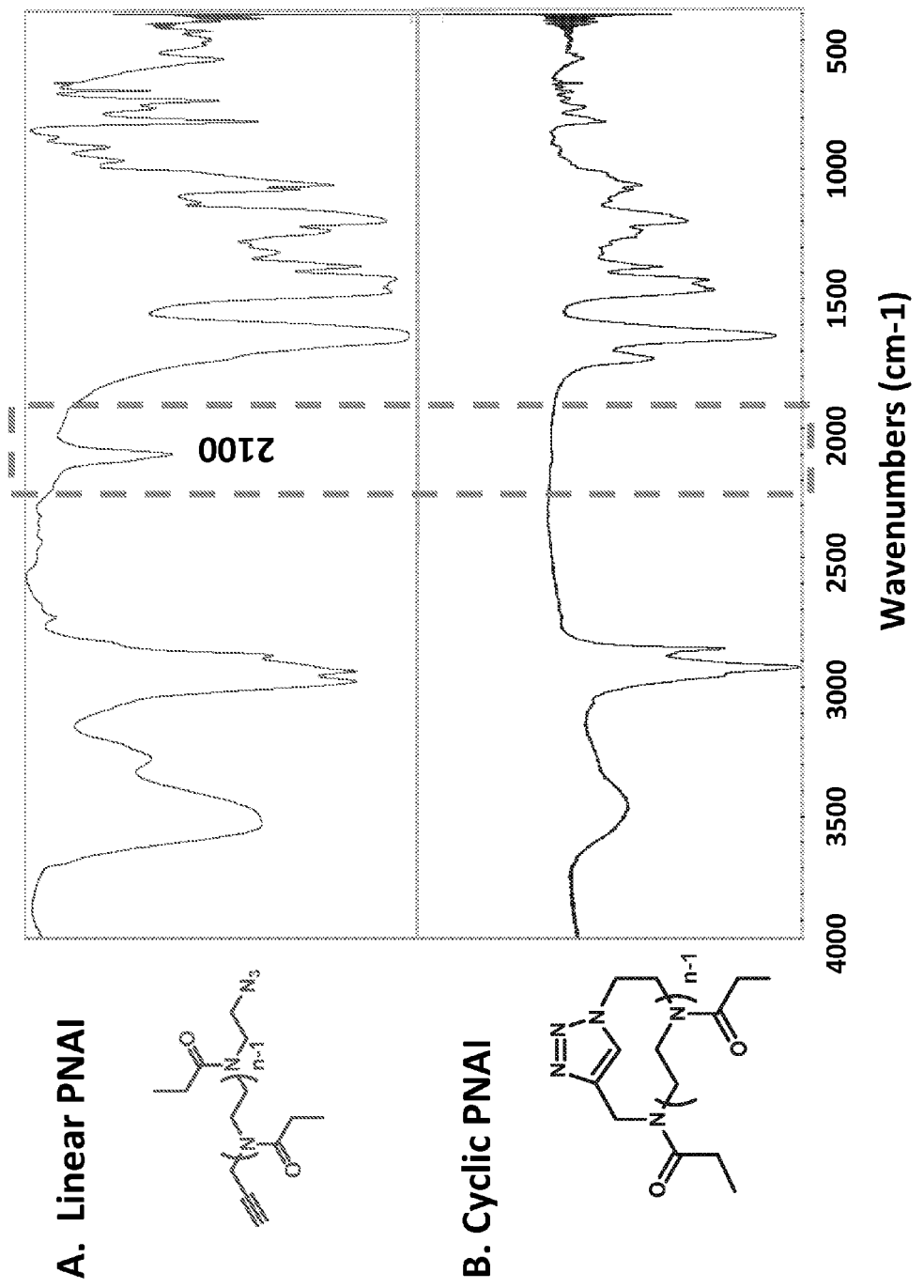
FIG. 7 shows the results of infrared (IR) spectroscopy of linear (lower trace) and cyclic (upper trace) PNAI. The absence of the azide resonance at 2100 cm$^{-1}$ (box) in the cyclic polymer gives evidence of the cyclization.
Figure 8:
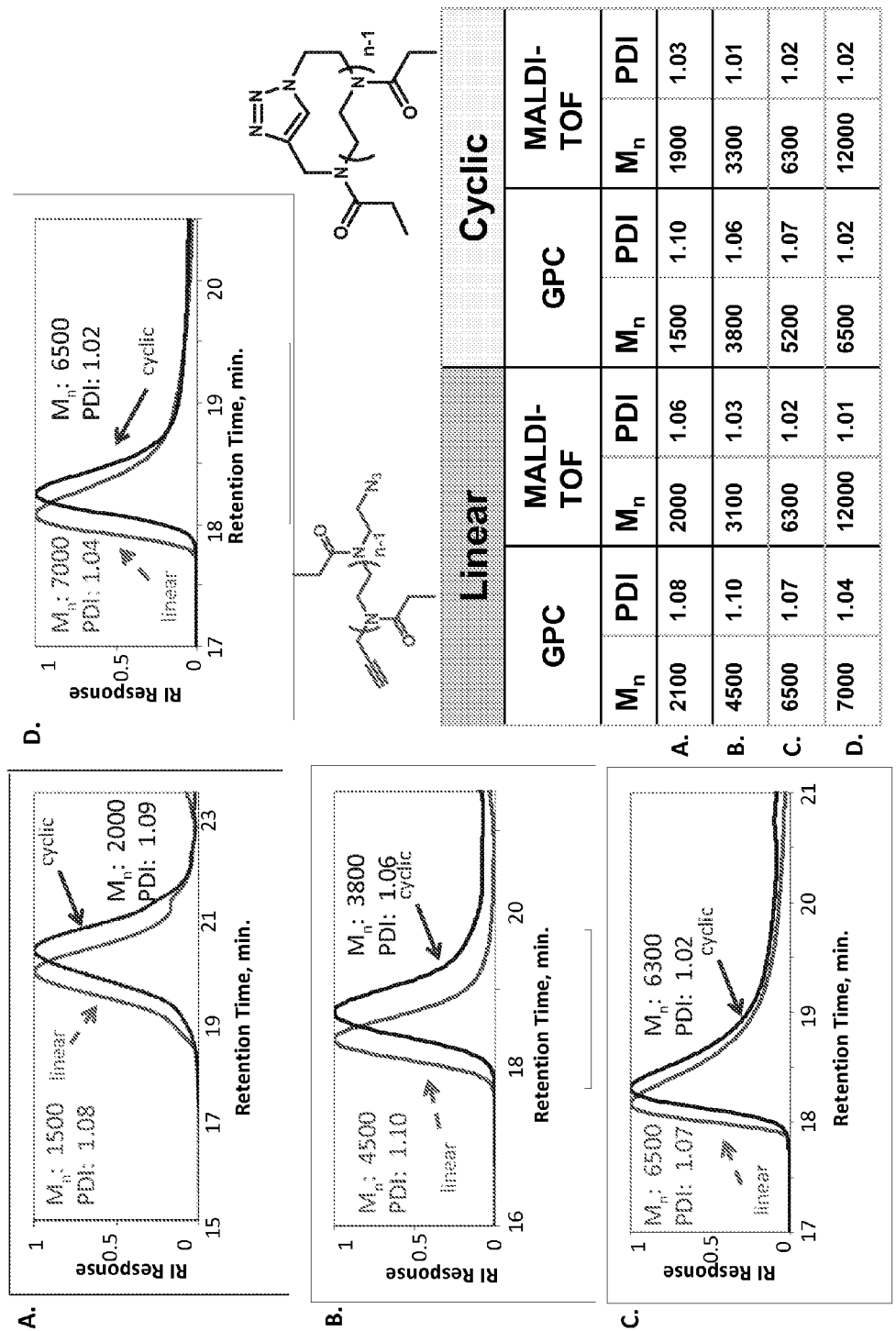
FIG. 8 is a representative example showing gel permeation chromatography (GPC) results of linear (dashed arrows, pointing to left-most trace for each of 8A through 8D) and cyclic (solid arrows, pointing to right-most trace of each of 8A through 8D) of different molecular weight PNAI.
Figure 9:
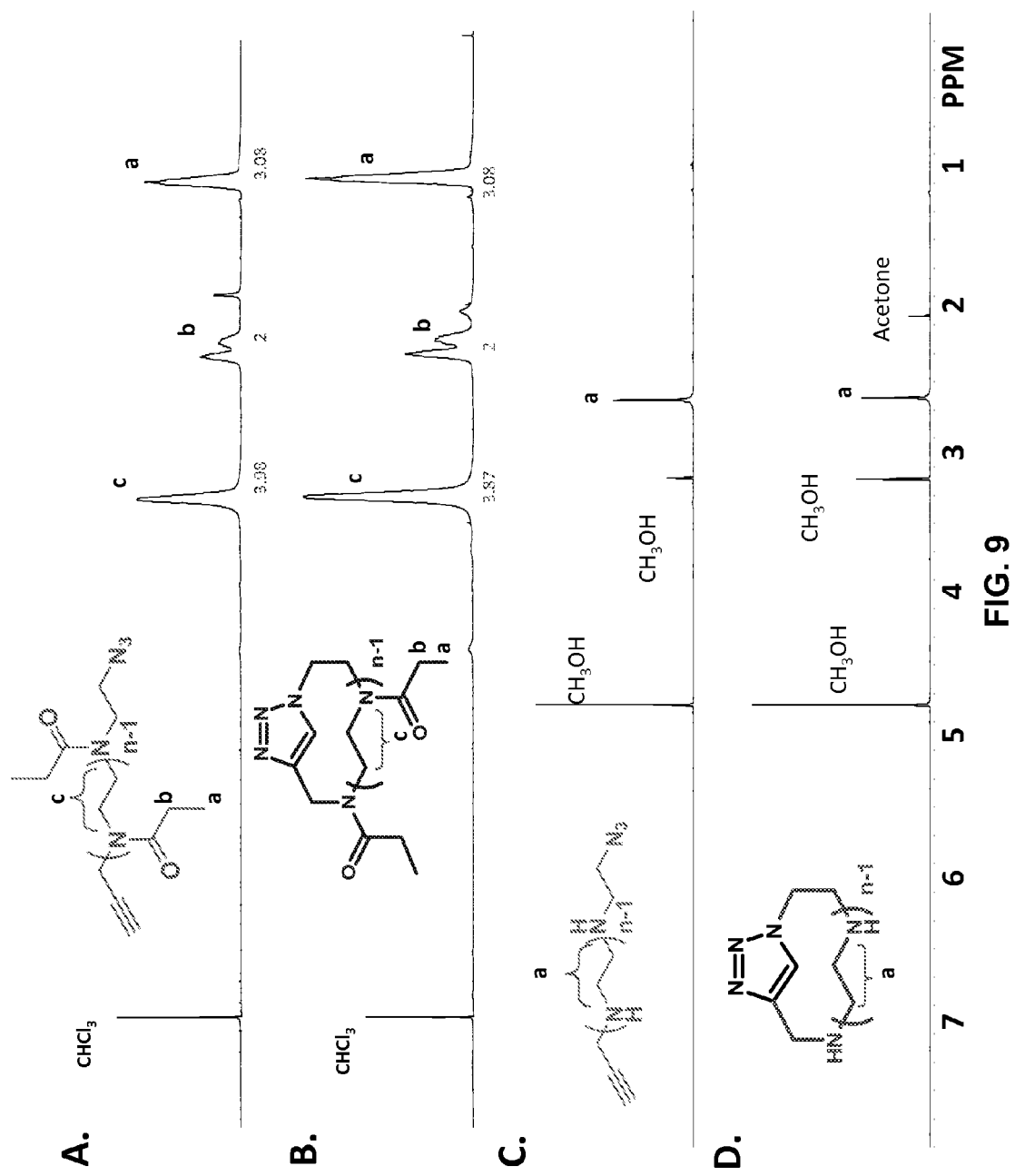
FIG. 9 shows $^1$H NMR of: 9A) linear PNAI; 9B) cyclic PNAI; 9C) linear PEI; and 9D) cyclic PEI.
Figure 10:
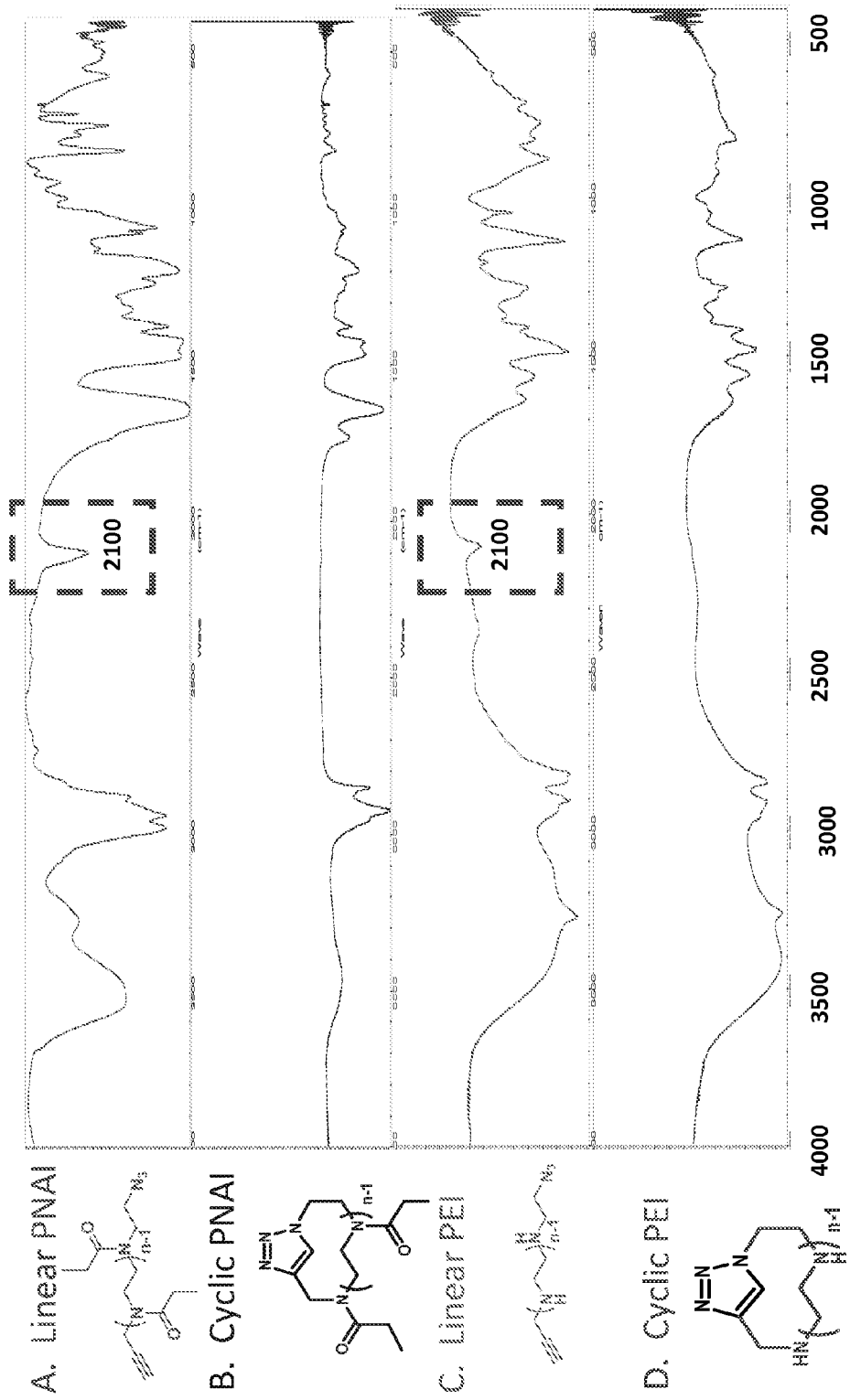
FIG. 10 shows results of IR spectroscopy of: 10A) linear PNAI; 10B) cyclic PNAI; 10C) linear PEI; and 10D) cyclic PEI. The absence of the azide resonance at 2100 cm$^{-1}$ in the cyclic polymers gives evidence of the cyclization.
Figure 11:
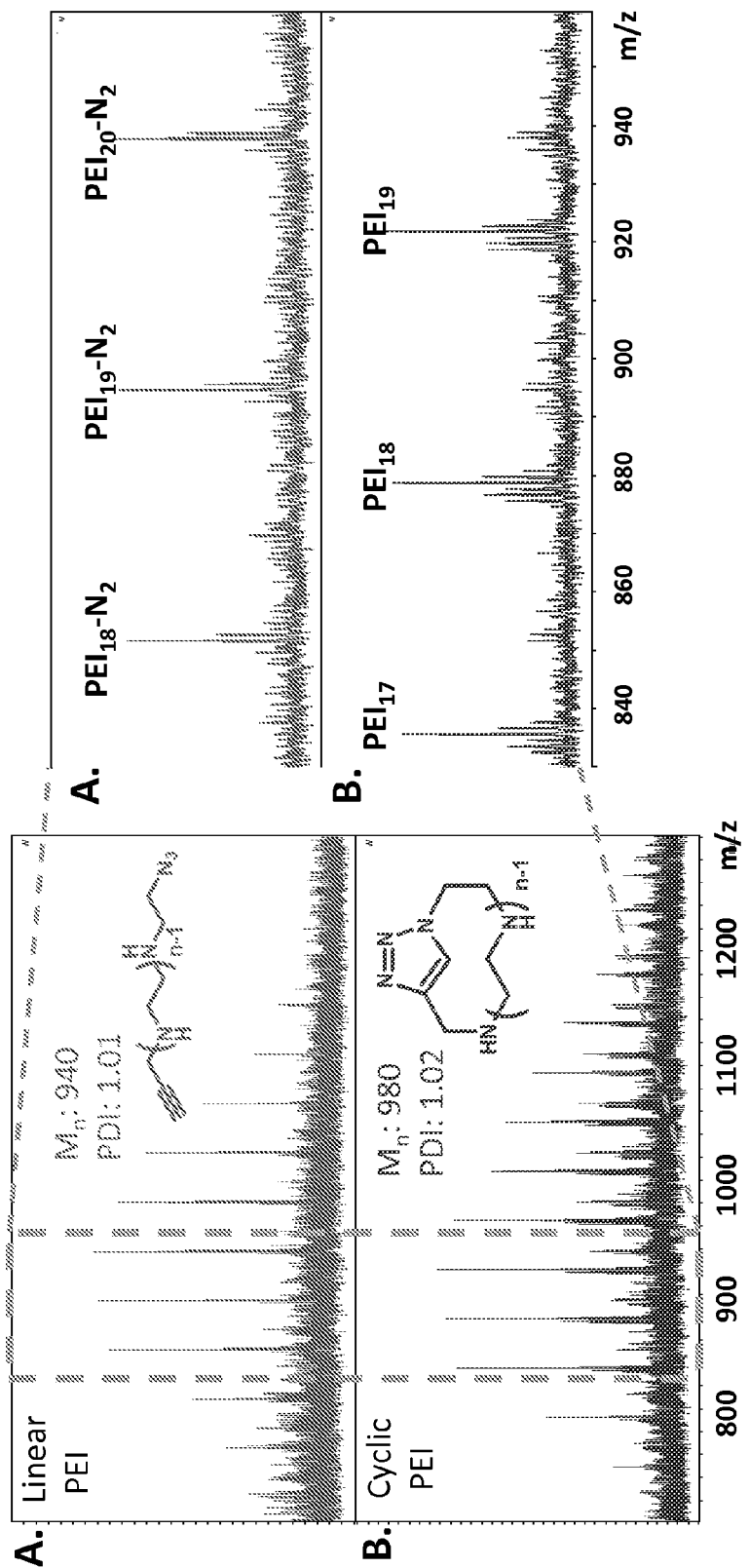
FIG. 11 is a representative example showing MALDI of: 11A) linear PEI; and 11B) cyclic PEI derived from the linear and cyclic PNAI shown in FIG. 8A. One may predict the expected molecular weight of linear and cyclic PEI from the molecular weight of the linear and cyclic PNAI from which it was synthesized. For linear PEI, predominately the loss of N$_2$ is observed in reflector mode. Once cyclized, the triazole ring negates the loss of N$_2$. The expected molecular weight of the hydrolyzed polymer suggests no degradation has occurred during the acid hydrolysis and no evidence is seen of the cyclic ring opening.
Figure 12:
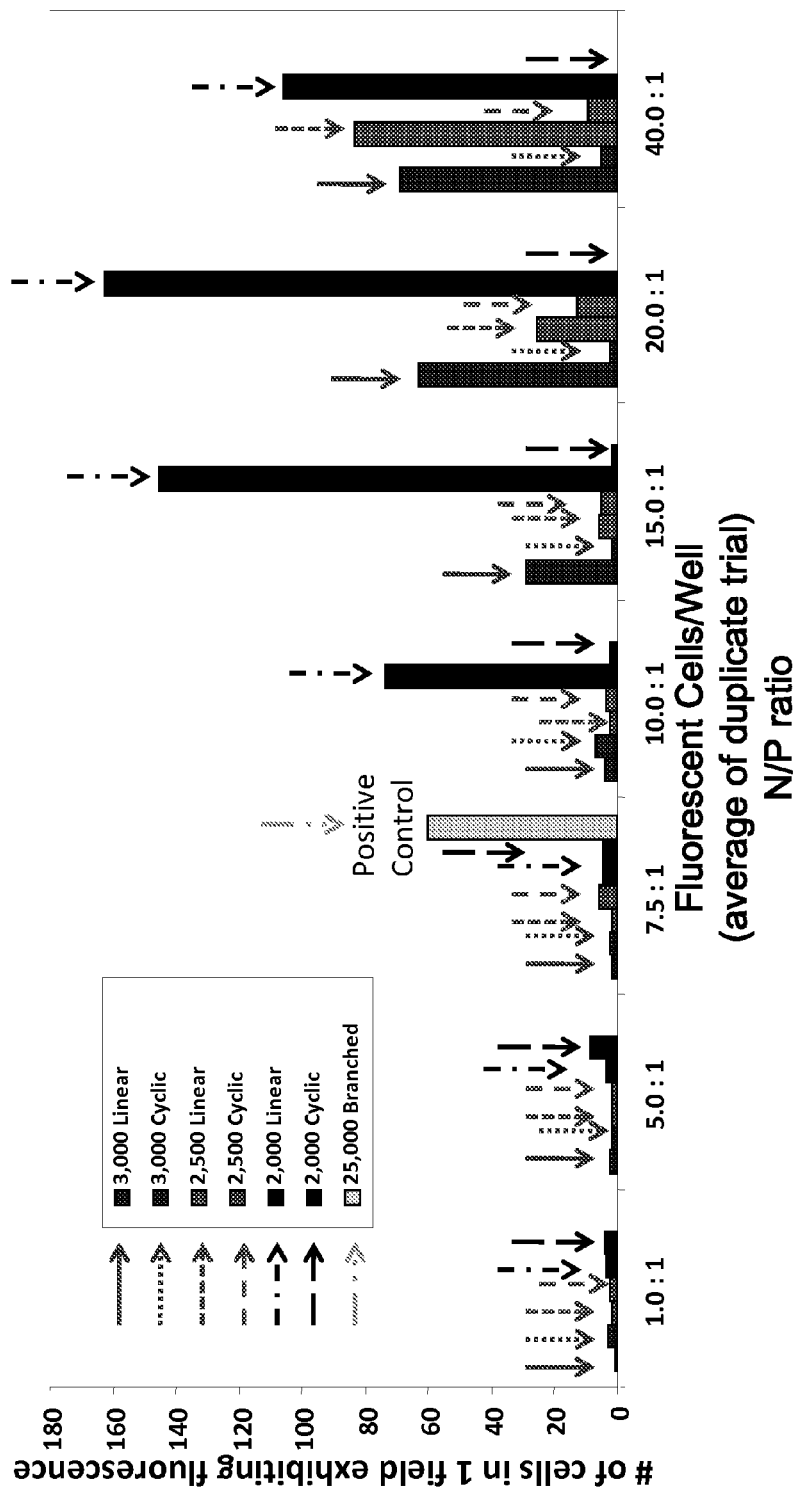
FIG. 12 shows initial comparative gene transfection study between linear and cyclic PEI of three different molecular weights, as measured by the number of cells in one field exhibiting fluorescence. A significant difference was observed between linear and cyclic PEI.

Once the cyclic PNAI was obtained, acid hydrolysis was used to synthesize cyclic PEI (Scheme 3; FIG. 3; EXAMPLE 5, below). In addition, linear PEI was synthesized with the linear analog of PNAI used to produce the cyclic PEI as a linear comparison. (Scheme 3; FIG. 3; EXAMPLE 4, below).

The variable "n" shown in FIGS. 1-3 may be an integer from about 1 to about 750, from about 1 to about 625, from about 1 to about 500, from about 1 to about 450, from about 1 to about 400, from about 1 to about 350, from about 1 to about 300, from about 1 to about 250, from about 1 to about 200, from about 1 to about 150, from about 1 to about 120, from about 1 to about 100, from about 1 to about 75, from about 1 to about 50, from about 1 to about 25, from about 1 to about 10, from about 1 to about 5, from about 10 to about 500, from about 10 to about 400, from about 10 to about 300, from about 10 to about 200, from about 10 to about 150, from about 10 to about 120, from about 10 to about 100, from about 10 to about 95, from about 10 to about 80, from about 10 to about 75, from about 10 to about 70, from about 10 to about 65, from about 10 to about 60, from about 10 to about 55, from about 10 to about 50, from about 10 to about 45, from about 10 to about 40, from about 10 to about 35, from about 10 to about 30, from about 10 to about 25, from about 10 to about 20, from about 25 to about 500, from about 25 to about 400, from about 25 to about 300, from about 25 to about 200, from about 25 to about 150, from about 25 to about 120, from about 25 to about 250, from about 25 to about 95, from about 25 to about 80, from about 25 to about 75, from about 25 to about 70, from about 25 to about 65, from about 25 to about 60, from about 25 to about 55, from about 25 to about 50, from about 25 to about 45, from about 25 to about 40, from about 25 to about 35, from about 25 to about 30, from about 100 to about 500, from about 150 to about 500, from about 200 to about 500, from about 250 to about 500, from about 300 to about 500, from about 350 to about 500, from about 400 to about 500, from about 450 to about 500, and preferably from about 25 to about 75.

Materials

N,N,N',N',N-Pentamethyldiethylenetriamine (PMDETA) and copper (I) bromide were used as purchased from Sigma-Aldrich (St. Louis, Mo.). Ethyl ether anhydrous and methylene chloride ($CHCl_2$) were used as purchased from Fisher Scientific (Fair Lawn, N.J.). Propargyl toluene-4-sulfonate was purchased from Fluka, stirred with $CaCO_3$, filtered, and placed over molecular sieves. Acetonitrile was purchased from Fisher Scientific, distilled over calcium hydride, and placed over molecular sieves. 2-ethyl-oxazoline purchased from Aldrich, distilled over calcium hydride, and placed over molecular sieves.

Instrumentation

Mass spectral data was acquired using a Bruker Autoflex III matrix-assisted laser desorption time of flight mass spectrometer (MALDI) with delayed extraction using the reflector and positive ion mode. MALDI-TOF MS samples of PNAI were prepared by the combination of PNAI (2 mg/mL) in THF, 1,8,9-Anthracenetriol (20 mg/mL) in chloroform, and KTFA (2 mg/mL) in THF at a ratio of 1:1:0.3. MALDI-TOF MS samples of PEI were prepared by the combination of PEI (10 mg/mL) in methanol and 1,8,9-Anthracenetriol (20 mg/mL) in chloroform with no additional counterion at a ratio of 0.2-0.5:1. $M_n$ and PDI for all polymers were calculated using PolyTools software. Size exclusion chromatography (GPC) was carried out on a Waters model 1515 series pump (Milford, Mass.) with three-column series from Polymer Laboratories, Inc. consisting of PLgel 5 μm Mixed C (300 mm×7.5 mm) and PLgel 5 μm 500 Å (300 mm×7.5 mm) columns. The system was fitted with a Model 2487 differential refractometer detector and anhydrous tetrahydrofuran was used as the mobile phase (1 mL/min flow rate). Infrared (IR) spectroscopy was implemented using a NEXUS 670 FT-IR E.S.P. (Madison, Wis.). Samples were made using approximately 4 mg of polymer and five 5 mg of KBr which was then ground into a fine powder by mortar and pestle and compacted into a pellet. All proton nuclear magnetic resonance (NMR) analysis was obtained from a 400 MHz Varian Mercury spectrometer (Palo Alto, Calif.), using TMS=0.00 ppm calibration and performed at room temperature with deuterated chloroform as the solvent. Microwave irradiation reactions were carried out using a Discover CEM Microwave Reactor (Matthews, N.C.).

EXAMPLE 1

Polymerization of poly(N-acylethylenimine) (PNAI)

PNAI was polymerized with propargyl toluene-4-sulfonate as the initiator to introduce an alkyne onto the polymer endgroup. Propargyl tosylate was stirred with $CaCO_3$ overnight to remove any free protons, filtered, and dried on the pump. A round bottom flask with magnetic stir bar attached to a condenser was flame dried to remove any water. Varying initiator to monomer ratios were used to target molecular weights between 1500 and 12000. For example, propargyl toluene-4-sulfonate (0.6053 mmol) and acetonitrile (5 mL) was added to the round bottom flask under $N_2$ gas and cooled in an ice bath. 2-ethyl-2-oxazoline (30.2633 mmol) was then added via syringe to the round bottom flask. The reaction mixture was stirred under nitrogen at 65° C. for 24 hours. The reaction was cooled in an ice bath followed by the addition $NaN_3$ to the reaction mixture and stirred for 30 minutes. The reaction was heated to 65° C. and allowed to stir overnight. The PNAI was precipitated in diethyl ether twice and washed with $NaHCO_3$. To isolate higher molecular weight polymer, further purification was performed by dissolving the polymer in 50% by volume of $CHCl_2$ and toluene (100 mL). Diethyl ether was added dropwise until cloudy. The solution was heated until clear and stored in a cold room overnight. The solvent was then decanted from the polymer. $^1$H NMR ($CDCl_3$): δ 1-1.2(b), 2.2-2.5(b), 3.2-3.6(b); $^{13}$C NMR ($CDCl_3$): δ 8-11(b), 25-27(b), 43-48(b); Representative Example: GPC: $M_n$: 7000 daltons, PDI: 1.04; MALDI-TOF MS: $M_n$: 12000 daltons, PDI; 1.01.

EXAMPLE 2

Polymerization of poly(N-acylethylenimine) (PNAI) (with Microwave Reactor)

PNAI was polymerized with propargyl toluene-4-sulfonate as the initiator to introduce an alkyne into the polymers. Propargyl tosylate was stirred with $CaCO_3$ overnight to remove any free protons, filtered, and dried on the pump. A microwave reaction vessel (8 mL) with magnetic stir bar was flame dried to remove any water, and filled with N₂ gas. Varying initiator to monomer ratios were used to target molecular weights between 1500 and 12000. For example, 2-ethyl-2-oxazoline (9.9062 mmol) and acetonitrile (1 mL) was added to the reaction vessel under N₂ gas and cooled in an ice bath. Propargyl toluene-4-sulfonate (0.9906 mmol) was added via syringe to the reaction vessel. The reaction mixture was reacted under microwave irradiation at 140° C. (120 watts) for 2.50 minutes. The reaction was removed from the microwave reactor and cooled in an ice bath. NaN₃ was added to the reaction mixture and stirred for 60 minutes under N₂ gas. The reaction mixture was reacted under microwave irradiation at 100° C. (120 watts) for 10 minutes and allowed to stir overnight to ensure complete termination with azide. The PNAI was then precipitated in diethyl ether and washed with NaHCO₃. ¹H NMR (CDCl₃): δ 1-1.2(b), 2.2-2.5(b), 3.2-3.6 (b); ¹³C NMR (CDCl₃): δ 8-11(b), 25-27(b), 43-48(b); Representative Example: GPC: M$_n$: 2100 daltons, PDI: 1.08; MALDI-TOF MS: M$_n$: 20000 daltons, PDI: 1.06.

The resulting linear PNAI corresponds to the structure of Formula 7 below:

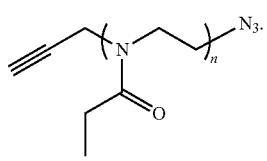

Formula 7

EXAMPLE 3

Cyclization of PNAI

A mass of 0.159 g of end group functionalized PNAI (0.018 mmol) was added to a 100 mL two neck round bottom flask containing a magnetic stir bar and then dissolved in 100 mL of CHCl₂. In a separate 250 mL two neck round bottom flask equip with a stir bar N,N,N',N',N-Pentamethyldiethylenetriamine (PMDETA) (0.211 g, 1.21 mmol) was dissolved into 120 mL of CHCl₂. Both reaction vessels were degassed three times via freeze pump thaw cycles during which time Cu(I)Br (0.159 g, 1.11 mmol) was added to the larger flask while frozen. Once thawed, a syringe pump with a 25 mL gas tight syringe was used to add the polymer/solvent solution to the 250 mL round bottom flask containing the Cu(I)Br/PMDETA/CHCl₂ solution at a rate of 2 mL/hr at room temperature. The syringe was filled periodically with the polymer/solvent solution until all solution was added. The reaction was then exposed to air and washed with a saturated solution of ammonium chloride (NH₄Cl) to remove any Cu. Further removal of Cu was preformed by passing the polymer through a plug of silica with MeOH as the eluent. The polymer was then passed through a 13 mm GD/X Disposable syringe filter (PTFE filter media; polypropeylene housing; 0.2 μm pore size) with THF. NMR (CDCl₃): δ 1-1.2(b), 2.2-2.5(b), 3.2-3.6(b); ¹³C NMR (CDCl₃): δ 8-11(b), 25-27(b), 43-48(b); Representative Example: GPC M$_n$: 4600 PDI: 1.08; MALDI-TOF MS: 4900 PDI: 1.02.

The cyclized PNAI corresponds to the structure of Formula 8 below:

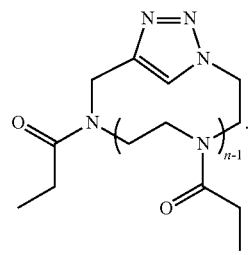

Formula 8

EXAMPLE 4

Optimized Cyclization Conditions for PNAI under 4K

A mass of 0.159 g of end group functionalized PNAI (1 mmol) was added to a 100 mL two neck round bottom flask containing a magnetic stir bar and then dissolved in 80 mL of CHCl₂. In a separate 250 mL two neck round bottom flask equip with a stir bar N,N,N',N',N-Pentamethyldiethylenetriamine (PMDETA) (0.422 g, 2.42 mmol) was dissolved into 120 mL of CHCl₂. Both reaction vessels were degassed three times via freeze pump thaw cycles during which time Cu(I)Br (0.302 g, 2.11 mmol) was added to the larger flask while frozen. Once thawed, a syringe pump with a 25 mL gas tight syringe was used to add the polymer/solvent solution to the 250 mL round bottom flask containing the Cu(I)Br/PMDETA/CHCl₂ solution at a rate of 2 mL/hr at room temperature. The syringe was filled periodically with the polymer/solvent solution until all solution was added. The reaction was then exposed to air and washed with a saturated solution of ammonium chloride (NH₄Cl) to remove any Cu. Further removal of Cu was preformed by passing the polymer through a plug of silica with MeOH as the eluent. The polymer was then passed through a 13 mm GD/X Disposable syringe filter (PTFE filter media; polypropeylene housing; 0.2 μm pore size) with THF. NMR (CDCl₃): δ 1-1.2(b), 2.2-2.5(b), 3.2-3.6(b); ¹³C NMR (CDCl₃): δ 8-11(b), 25-27(b), 43-48(b); Representative Example: GPC M$_n$: 1500 PDI: 1.10; MALDI: M$_n$: 1900 PDI: 1.03.

EXAMPLE 5

Acid Hydrolysis of Linear PNAI to Linear PEI

Linear PNAI (48 g/L) was dissolved in 16.8 wt % HCl (14.25 mL HCL in 83.2 mL H₂O) reacted under reflux for 24 hours. The reaction was then cooled to room temperature and the acid solution was evaporated. Fresh deionized water was then added and the solution was neutralized with 2.5 M NaOH solution to a pH>8. The precipitated PEI was then filtered, washed with DI water, dissolved in methanol, and precipitated in diethyl ether. ¹H NMR (methanol-d): 2.6-2.8 (b); Representative Example: MALDI-TOF MS: M$_n$: 940 PDI: 1.01.

The resulting linear PEI corresponds to the structure of Formula 9 below:

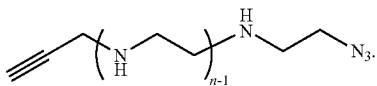

Formula 9

EXAMPLE 6

Acid Hydrolysis of Cyclic PNAI to PEI

Cyclic PNAI (48 g/L) was dissolved in 16.8 wt % HCl (14.25 mL HCL in 83.2 mL $H_2O$) reacted under reflux for 24 hours. The reaction was then cooled to room temperature and the acid solution was evaporated. Fresh deionized water was then added and the solution was neutralized with 2.5 M NaOH solution to a pH>8. The precipitated PEI was then filtered, washed with deionized water, dissolved in methanol, and precipitated in diethyl ether. $^1$H NMR (methanol-d): 2.6-2.8(b). Representative Example: MALDI-TOF MS: $M_n$: 980 PDI: 1.02.

The cyclized PEI corresponds to the structure of Formula 10 below:

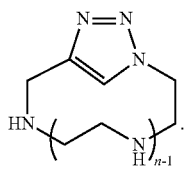

Formula 10

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A compound selected from the group consisting of:

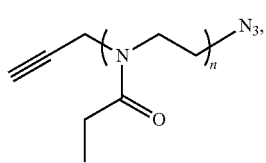

Formula 7

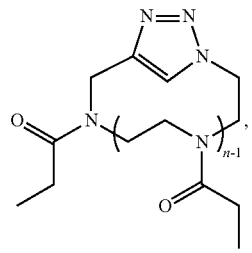

Formula 8

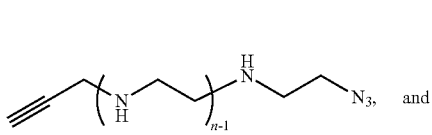

Formula 9

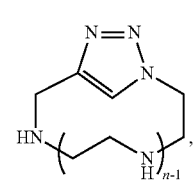

Formula 10 wherein, for formulas 7, 8, and 10, n is an integer from 1 to 750, and for formula 9, n is an integer from 10 to 750.

2. The compound of claim 1, wherein said compound corresponds to Formula 7.

3. The compound of claim 1, wherein said compound corresponds to Formula 8.

4. The compound of claim 1, wherein said compound corresponds to Formula 9.

5. The compound of claim 1, wherein said compound corresponds to Formula 10.

6. A method of producing a linear PNAI, the method comprising:
   a) combining propargyl toluene-4-sulfonate with 2-ethyl-2-oxazoline; and
   b) adding sodium azide to said combination,
   thereby producing said linear PNAI.

7. A method of producing a cyclic PNAI, the method comprising:
   a) precipitating the linear PNAI of claim 6; and
   b) adding said precipitated linear PNAI to a Cu(I)Br/PMDETA/$CHCl_2$ solution,
   thereby producing cyclic PNAI.

8. A method of producing a linear PEI, the method comprising:
   a) precipitating the linear PNAI of claim 6; and
   b) performing acid reflux of said-linear PNAI,
   thereby producing a linear PEI.

9. A method of producing a cyclic PEI, the method comprising:
   a) producing a cyclic PNAI as provided in claim 7; and
   b) performing acid reflux of said cyclic PNAI,
   thereby producing a cyclic PEI.

10. A method of introducing a substance into a cell, the method comprising:

a) mixing said substance with:

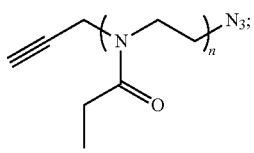

Formula 7

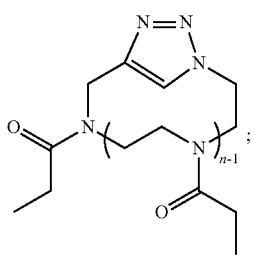

Formula 8

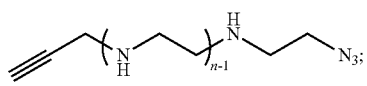

Formula 9

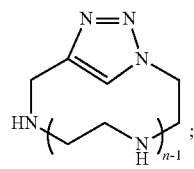

Formula 10 or v) a combination thereof;

wherein, for formulas 7, 8, and 10, n is an integer from 1 to 750, and for formula 9, n is an integer from 10 to 750; and b) exposing said cell to said mixture, thereby introducing said substance into said cell.

11. The method of claim 10, wherein said substance is a nucleic acid sequence.

12. The method of claim 11, wherein said introducing effects the expression of a protein encoded by said nucleic acid sequence.

13. The method of claim 11, wherein said introducing suppresses the expression of a protein.

14. The method of claim 10, wherein said substance is a drug.

15. The method of claim 10, wherein said cell is a prokaryotic cell.

16. The method of claim 10, wherein said cell is a eukaryotic cell.

17. The method of claim 10, wherein said substance is mixed with the compound of Formula 7.

18. The method of claim 10, wherein said substance is mixed with the compound of Formula 8.

19. The method of claim 10, wherein said substance is mixed with the compound of Formula 9.

20. The method of claim 10, wherein said substance is mixed with the compound of Formula 10.

21. The method of claim 10, wherein said substance is mixed with a combination of the compounds of Formulae 7, 8, 9, and 10.

22. The compound of claim 1, wherein n is an integer from 10 to 500.

* * * * *